United States Patent [19]
Kalnes et al.

[11] Patent Number: 5,849,979
[45] Date of Patent: *Dec. 15, 1998

[54] PROCESS FOR COOLING A HOT VAPOR EFFLUENT OF A HYDROCARBON DEHYDROGENATION ZONE AND REMOVING TRACE QUANTITIES OF POLYNUCLEAR AROMATIC COMPOUNDS

[75] Inventors: Tom N. Kalnes, La Grange; Bryan K. Glover, Algonquin; Lester F. Smith, Itasca; Norman H. Scott, Arlington Heights, all of Ill.

[73] Assignee: UOP LLC, Des Plaines, Ill.

[ * ] Notice: The term of this patent shall not extend beyond the expiration date of Pat. No. 5,481,060.

[21] Appl. No.: 812,800

[22] Filed: Mar. 6, 1997

[51] Int. Cl.⁶ .................................................. C07C 7/11
[52] U.S. Cl. ........................ 585/809; 585/655; 585/867
[58] Field of Search ................... 585/804, 807, 585/809, 867, 655

[56] References Cited

U.S. PATENT DOCUMENTS

| | | | |
|---|---|---|---|
| 2,367,479 | 1/1945 | Wolk | 260/680 |
| 2,451,050 | 10/1948 | Tonberg | 260/681.5 |
| 2,905,734 | 9/1959 | Davidson et al. | 260/683 |
| 3,793,389 | 2/1974 | Oleszko et al. | 260/679 R |
| 3,796,768 | 3/1974 | Starzenski et al. | 260/683 R |
| 4,430,517 | 2/1984 | Imai et al. | 585/660 |
| 5,300,715 | 4/1994 | Vora | 585/254 |
| 5,481,060 | 1/1996 | Scott et al. | 585/867 |

FOREIGN PATENT DOCUMENTS

| | | |
|---|---|---|
| 4046302 | 6/1970 | Japan . |
| 2124836 | 11/1988 | Japan . |
| 27908 | of 1906 | United Kingdom . |

*Primary Examiner*—Glenn Caldarola
*Assistant Examiner*—Thuan D. Dang
*Attorney, Agent, or Firm*—Thomas K. McBride; John G. Tolomei; John G. Cutts, Jr.

[57] ABSTRACT

A process for the removal of trace quantities of polynuclear aromatic compounds from the vapor effluent of a hydrocarbon dehydrogenation zone containing normally gaseous olefinic hydrocarbons, trace mononuclear aromatic compounds and trace polynuclear aromatic compounds by contacting the hot vapor effluent of a hydrocarbon dehydrogenation zone with a cold lean liquid absorption stream to absorb at least a portion of the trace polynuclear aromatic compounds to produce a rich liquid absorption stream and a gaseous olefin-containing hydrocarbon stream having a reduced concentration of polynuclear aromatic compounds.

11 Claims, 1 Drawing Sheet

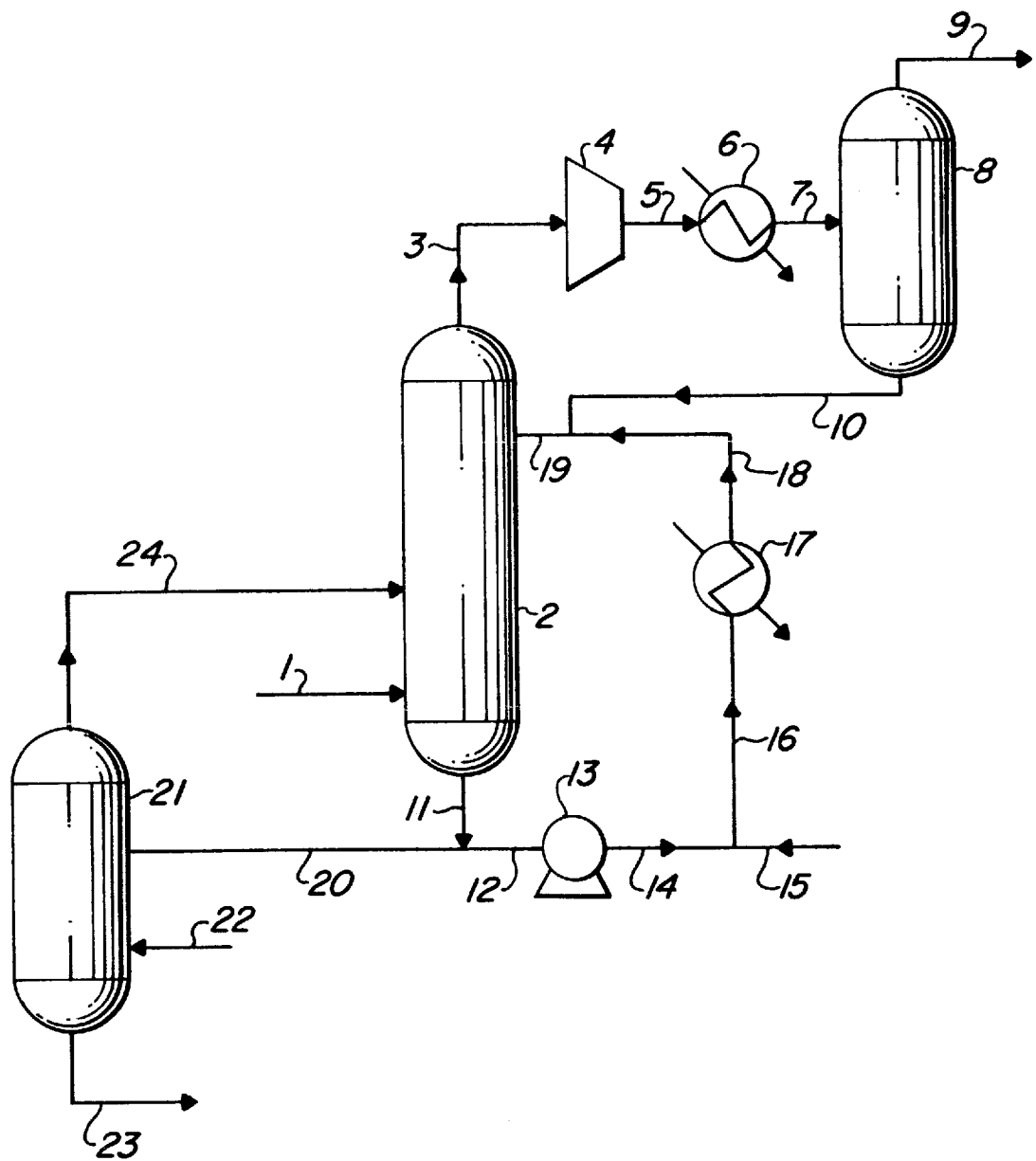

PROCESS FOR COOLING A HOT VAPOR EFFLUENT OF A HYDROCARBON DEHYDROGENATION ZONE AND REMOVING TRACE QUANTITIES OF POLYNUCLEAR AROMATIC COMPOUNDS

FIELD OF THE INVENTION

The field of art to which this invention pertains is the cooling of a hot vapor effluent from a normally gaseous hydrocarbon dehydrogenation reaction zone and the recovery and removal of heavy hydrocarbonaceous co-products including polynuclear aromatic compounds.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater severity operation of existing commercial facilities has highlighted the problem which occurs in the product recovery section of hydrocarbon dehydrogenation processes. This problem is the result of the co-production of trace quantities of polynuclear aromatic compounds. The polynuclear aromatic compounds are considered to be an undesired impurity and present a severe operational problem because when they condense and plate out on the cooler surfaces of the plant there are detrimental results. The deposits of polynuclear aromatic compounds are difficult to remove, they reduce the efficiency of heat exchangers and they may eventually lead to plugging. In addition, when polynuclear aromatic compounds are carried to downstream processing units, they contaminate the resulting products and prevent the obtention of product specifications such as color, for example.

U.S. Pat. No. 5,481,060 issued to Scott et al discloses the removal of trace quantities of polynuclear aromatic compounds from the vapor effluent of a hydrocarbon dehydrogenation zone containing normally gaseous olefinic hydrocarbons, trace mononuclear aromatic compounds and trace polynuclear aromatic compounds.

Therefore, those skilled in the art of hydrocarbon processing have sought methods to overcome the problem posed by the production of polynuclear aromatic compounds in dehydrogenation production facilities. The process of the present invention provides a facile and economical solution to the problem of the co-production of polynuclear aromatic compounds in a dehydrogenation plant.

BRIEF SUMMARY OF THE INVENTION

The present invention relates to a process for the simultaneous cooling of the vapor effluent from a hydrocarbon dehydrogenation zone containing normally gaseous olefinic hydrocarbons and trace quantities of mononuclear and polynuclear aromatic compounds and the removal of the polynuclear aromatic compounds from the gaseous olefinic hydrocarbons. The cooling and removal of polynuclear aromatic compounds is performed by directly contacting the hot vapor effluent from a hydrocarbon dehydrogenation zone with a cold lean liquid absorption stream.

One embodiment of the present invention may be characterized as a process for cooling a hot vapor effluent of a hydrocarbon dehydrogenation zone comprising normally gaseous olefinic hydrocarbons and trace polynuclear aromatic compounds and removing trace quantities of polynuclear aromatic compounds from the hot vapor effluent which process comprises: (a) contacting the hot vapor effluent of a hydrocarbon dehydrogenation zone with a cold lean liquid absorption stream having a temperature less than the hot vapor effluent to cool the hot vapor effluent to a temperature less than about 120° F. and to absorb at least a portion of the trace polynuclear aromatic compounds in a cooling/absorption zone to produce a cooled gaseous olefinic hydrocarbon stream having a reduced concentration of polynuclear aromatic compounds and a rich liquid absorption stream having a temperature greater than about 120° F.; (b) recovering the cooled gaseous olefin-containing hydrocarbon stream having a reduced concentration of polynuclear aromatic compounds; and (c) cooling at least a portion of the rich liquid absorption stream from step (a) to provide at least a portion of the cold lean liquid absorption stream.

Another embodiment of the present invention may be characterized as a process for cooling a hot vapor effluent of a hydrocarbon dehydrogenation zone comprising normally gaseous olefinic hydrocarbons and trace polynuclear aromatic compounds and removing trace quantities of polynuclear aromatic compounds from the hot vapor effluent which process comprises: (a) contacting the hot vapor effluent of a hydrocarbon dehydrogenation zone in a countercurrent vapor-liquid absorption zone with a cold lean liquid absorption stream having a temperature less than the hot vapor effluent to cool the hot vapor effluent to a temperature less than about 120° F. and to absorb at least a portion of the trace polynuclear aromatic compounds to produce a cooled gaseous olefinic hydrocarbon stream having a reduced concentration of polynuclear aromatic compounds and a rich liquid absorption stream having a temperature greater than about 120° F.; (b) recovering the cooled gaseous olefin-containing hydrocarbon stream having a reduced concentration of polynuclear aromatic compounds; (c) cooling at least a portion of the rich liquid absorption stream from step (a) to provide at least a portion of the cold lean liquid absorption stream; (d) separating at least a portion of the rich liquid absorption stream from step (a) to produce a stream comprising polynuclear aromatic compounds and a stream having a reduced concentration of polynuclear aromatic compounds; and (e) introducing the stream having a reduced concentration of polynuclear aromatic compounds from step (d) into the countercurrent vapor-liquid absorption zone.

Yet another embodiment of the present invention may be characterized as a process for cooling a hot vapor effluent of a hydrocarbon dehydrogenation zone comprising normally gaseous olefinic hydrocarbons, trace polynuclear aromatic compounds and trace mononuclear aromatic compounds and removing trace quantities of polynuclear aromatic compounds from the hot vapor effluent which process comprises: (a) contacting the hot vapor effluent of a hydrocarbon dehydrogenation zone in a countercurrent vapor-liquid absorption zone with a cold lean liquid absorption stream having a temperature less than the hot vapor effluent to cool the hot vapor effluent to a temperature less than about 120° F. and to absorb at least a portion of the trace polynuclear aromatic compounds to produce a cooled gaseous olefinic hydrocarbon stream having a reduced concentration of polynuclear aromatic compounds and comprising trace mononuclear aromatic compounds and a rich liquid absorption stream having a temperature greater than about 120° F.; (b) compressing and cooling the cooled gaseous olefin-containing hydrocarbon stream having a reduced concentration of polynuclear aromatic compounds and comprising trace mononuclear aromatic compounds to produce a liquid stream comprising mononuclear aromatic compounds and a gaseous olefin-containing hydrocarbon stream having a reduced concentration of polynuclear aromatic compounds; (c) introducing the liquid stream comprising mononuclear aromatic compounds from step (c) into the countercurrent vapor-liquid absorption zone; (d) recovering the gaseous olefin-containing hydrocarbon stream having a reduced concentration of polynuclear aromatic compounds from step (b); (e) cooling at least a portion of the rich liquid absorption stream from step (a) to provide at least a portion of the cold lean liquid absorption stream; (f) separating at least a portion of the rich liquid absorption stream from step (a) to produce a stream comprising polynuclear aromatic compounds and a stream having a reduced concentration of polynuclear aromatic compounds; and (g) introducing the stream having a reduced concentration of polynuclear aromatic compounds from step (f) into the countercurrent vapor-liquid absorption zone.

Other embodiments of the present invention encompass further details such as preferred absorption solutions and preferred operating conditions.

The process of the present invention provides the advantages of using inexpensive and efficient absorption solutions to serve as a liquid absorption stream and a direct contact cooling medium which isolates troublesome polynuclear-aromatic compounds and eliminates the need for process heat exchangers which are susceptible to fouling and plugging.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the cooling of the vapor effluent from a hydrocarbon dehydrogenation zone containing normally gaseous olefinic hydrocarbons and the recovery of polynuclear aromatic compounds from the vapor effluent of a hydrocarbon dehydrogenation zone. The dehydrogenation of paraffinic hydrocarbons is well known to those skilled in the art of hydrocarbon processing.

In the dehydrogenation process, fresh hydrocarbon feed is combined with recycle hydrogen and unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream of olefinic hydrocarbons. In accordance with the present invention, the effluent from the catalytic reaction zone contains unconverted saturated hydrocarbons, olefin hydrocarbons, mononuclear aromatic compounds in an amount from about 100 to about 5,000 wppm and polynuclear aromatic compounds in an amount from about 50 to about 500 wppm.

In accordance with the present invention, the dehydrogenation reaction zone vapor effluent is preferably heat-exchanged with the incoming feed to the dehydrogenation reaction zone to cool the dehydrogenation zone effluent to a temperature in the range from about 200° F. to about 400° F. This temperature range is above the dew point of the polynuclear aromatic compounds and therefore the traditional combined feed-effluent heat exchanger may be used without any danger of significant fouling or plugging. Once the dehydrogenation zone vapor effluent is cooled to a temperature between about 200° F. and 400° F., the effluent is introduced into a combination cooling and absorption zone to contact a cold liquid absorption stream in order to cool the dehydrogenation zone vapor effluent to a temperature in the range from about 50° F. (10° C.) to about 150° F. (65° C.) and to separate and recover the trace quantities of polynuclear aromatic compounds which are contained in the dehydrogenation reaction zone effluent. A preferred cooling and absorption zone is a countercurrent vapor-liquid absorption zone.

The resulting cooled and scrubbed dehydrogenation reaction zone effluent vapor may then be compressed, cooled, routed to a vapor-liquid separator, treated for chloride removal, treated for water removal, subjected to cryogenic refrigeration or fractionated, for example.

The liquid absorption and cooling medium may comprise any suitable compound or component which is capable of being cooled and circulated to perform the cooling function and of being able to absorb polynuclear aromatic compounds to perform the absorption function. A preferred absorption and cooling medium comprises a petroleum fraction boiling in the range of about 400° F. (204° C.) to about 700° F. (371° C.) and may include, for example, a component selected from the group consisting of kerosene, gas oil, diesel oil, light cycle oil (LCO) which is a product from a fluid catalytic cracking (FCC) process and admixtures thereof.

In another preferred embodiment, after the effluent from the hydrocarbon dehydrogenation zone has been cooled and contacted with the lean liquid absorption liquid, the resulting gaseous olefinic hydrocarbon stream is compressed to a pressure in the range from about 30 psig (207 kPa gauge) to about 200 psig (1379 kPa gauge), and cooled to a temperature in the range from about 85° F. (29° C.) to about 150° F. (65° C.), and introduced into a vapor-liquid separation zone. A liquid stream is removed from the vapor-liquid separation zone and is preferably recycled back to the cooling and contacting zone.

Subsequently a vapor stream containing olefinic hydrocarbons is removed from the vapor-liquid separation zone and further chilled to a temperature in the range of about 0° F. (−18° C.) to about 100° F. (38° C.) and introduced into a chilled vapor-liquid separation zone. A liquid stream is removed from the chilled vapor-liquid separation zone and may also be introduced into the cooling and absorption zone. The vapor stream leaving the chilled vapor-liquid separation zone is essentially free of polynuclear aromatic compounds. Preferably, the vapor stream contains less than about 1 wppm polynuclear aromatic compounds.

In accordance with the present invention, at least a portion of the rich liquid absorption stream is preferably separated to produce a stream comprising polynuclear aromatic compounds and a stream having a reduced concentration of polynuclear aromatic compounds. This separation is preferably conducted by introducing the rich liquid absorption stream into a stripper to contact a hot hydrogen-rich gaseous stream. The overhead from the stripper comprises hydrogen, gaseous olefinic hydrocarbons and gaseous paraffinic hydrocarbons, and is preferably routed back to the cooling and absorption zone. The stripper bottoms comprise essentially all of the polynuclear aromatic compounds introduced with the vapor effluent of the hydrocarbon dehydrogenation zone.

DETAILED DESCRIPTION OF THE DRAWING

With reference now to the drawing, a vapor effluent from a hydrocarbon dehydrogenation zone containing normally gaseous olefinic hydrocarbons, trace mononuclear aromatic compounds and trace polynuclear aromatic compounds is introduced into the process via conduit 1 and enters cooling/absorption zone 2. The vapor effluent is contacted in cooling/absorption zone 2 with a hereinafter-described cold lean absorption liquid in order to cool and remove essentially all of the trace polynuclear aromatic compounds and at least a portion of the trace mononuclear aromatic compounds. A resulting vapor stream is removed from cooling/absorption zone 2 via conduit 3 and introduced into compressor 4. The resulting compressed gas is removed from compressor 4 via conduit 5 and is cooled in heat exchanger 6. A resulting two-phase stream is removed from heat exchanger 6 via conduit 7 and is introduced into vapor-liquid separator 8. A resulting vapor stream is removed from vapor-liquid separator 8 via conduit 9 and recovered. A liquid stream is removed from vapor-liquid separator 8 via conduit 10 and is introduced via conduit 19 into cooling/absorption zone 2. A rich liquid absorption stream is removed from cooling/absorption zone 2 via conduit 11 and at least a portion is transported via conduit 12, passed through pump 13, transported via conduit 14 and admixed with a fresh light cycle oil introduced via conduit 15. The resultant mixture of recycle absorption liquid and fresh make-up absorption liquid is transported via conduit 16 and introduced into heat exchanger 17. The resulting cool absorbent liquid is removed from heat exchanger 17 and transported via conduits 18 and 19 and introduced into cooling/absorption zone 2. At least another portion of the absorbent liquid which is removed via conduit 11 from cooling/absorption zone 2 is transported via conduit 20 and introduced into stripping zone 21. A hot hydrogen-rich gaseous stream is introduced via conduit 22 into stripping zone 21. A gaseous stream containing hydrogen, normally gaseous hydrocarbons and mononuclear aromatic compounds is removed from stripping zone 21 via conduit 24 and is introduced into cooling/absorption zone 2. A liquid stream containing spent absorbent and comprising polynuclear aromatic compounds is removed from stripping zone 21 via conduit 23 and recovered. The cool absorbent liquid stream transported via conduits 18 and 19 as described hereinabove serves as the hereinabove-described cold lean absorption liquid.

The process of the present invention is further demonstrated by the following illustrative embodiment. This illustrative embodiment is, however, not presented to unduly limit the process of this invention, but to further illustrate the advantages of the hereinabove-described embodiment. The following data were not obtained by the actual performance of the present invention, but are considered prospective and reasonably illustrative of the expected performance of the invention based upon sound engineering calculations.

ILLUSTRATIVE EMBODIMENT

An effluent from an isobutane dehydrogenation zone in an amount of 290,000 pounds per hour and at a temperature of about 285° F. and a pressure of about 3 psig is introduced into a countercurrent cooling/absorption zone and is contacted with a cold lean liquid absorber solution circulating in an amount of about 1,000,000 pounds per hour and a temperature of 93° F. in a cooler/absorber vessel. A light cycle oil (LCO) in an amount of 255 pounds per hour is added to the circulating lean liquid absorber solution as make-up. A cooled gaseous stream having a temperature of 100° F. in an amount of about 290,000 pounds per hour and containing essentially no polynuclear aromatic compounds is removed from the cooler/absorber vessel, compressed to a pressure of about 90 psig and cooled to about 95° F. A liquid stream in the amount of 5,000 pounds per hour is separated from the previous compression and cooling and is recycled to the cooler/absorber vessel. A liquid slipstream from the bottoms of the cooler/absorber vessel having a temperature of 170° F. in the amount of 600 pounds per hour is stripped with about 250 pounds per hour of hydrogen gas to remove normally gaseous hydrocarbons before the liquid slipstream is removed from the process. The vapor leaving the stripper is recycled to the cooler/absorber vessel.

The foregoing description and illustrative embodiment clearly illustrate the advantages encompassed by the method of the present invention and the benefits to be afforded with the use thereof.

What is claimed:

1. A process for cooling a hot vapor effluent of a hydrocarbon dehydrogenation zone having a temperature greater than about 200° F. and comprising normally gaseous olefinic hydrocarbons and trace polynuclear aromatic compounds and removing trace quantities of polynuclear aromatic compounds from said hot vapor effluent which process comprises:

(a) contacting said hot vapor effluent of a hydrocarbon dehydrogenation zone with a cold lean liquid absorption stream having a temperature less than said hot vapor effluent to cool said hot vapor effluent to a temperature less than about 120° F. and to absorb at least a portion of said trace polynuclear aromatic compounds in a cooling/absorption zone to produce a cooled gaseous olefinic hydrocarbon stream having a reduced concentration of polynuclear aromatic compounds and a rich liquid absorption stream having a temperature greater than about 120° F.;

(b) recovering said cooled gaseous olefin-containing hydrocarbon stream having a reduced concentration of polynuclear aromatic compounds; and (c) cooling at least a portion of said rich liquid absorption stream from step (a) to provide at least a portion of said cold lean liquid absorption stream.

2. The process of claim 1 wherein at least a portion of said rich liquid absorption stream from step (a) is separated to produce a stream comprising polynuclear aromatic compounds and a stream having a reduced concentration of polynuclear aromatic compounds.

3. The process of claim 1 wherein said normally gaseous olefinic hydrocarbons are selected from the group consisting of ethylene, propylene and butylene.

4. The process of claim 1 wherein the trace quantities of polynuclear aromatic compounds are present in the hot vapor effluent of the dehydrogenation zone in an amount from about 50 to about 500 wppm.

5. The process of claim 1 wherein said cooling/absorption zone is a countercurrent vapor-liquid absorption zone.

6. The process of claim 1 wherein said gaseous olefin-containing hydrocarbon stream having a reduced concentration of polynuclear aromatic compounds contains less than about 1 wppm polynuclear aromatic compounds.

7. The process of claim 1 wherein said cold lean liquid absorption stream comprises a petroleum fraction boiling in the range of about 400° F. (204° C.) to about 700° F. (371° C.).

8. The process of claim 1 wherein said cold lean liquid absorption stream comprises a component selected from the group consisting of kerosene, gas oil, diesel oil, light cycle oil and admixtures thereof.

9. The process of claim 1 wherein said cold lean liquid absorption stream has a temperature in the range from about 90° F. to about 120° F.

10. A process for cooling a hot vapor effluent of a hydrocarbon dehydrogenation zone having a temperature greater than about 200° F. and comprising normally gaseous olefinic hydrocarbons and trace polynuclear aromatic compounds and removing trace quantities of polynuclear aromatic compounds from said hot vapor effluent which process comprises:

(a) contacting said hot vapor effluent of a hydrocarbon dehydrogenation zone in a countercurrent vapor-liquid absorption zone with a cold lean liquid absorption stream having a temperature less than said hot vapor effluent to cool said hot vapor effluent to a temperature less than about 120° F. and to absorb at least a portion of said trace polynuclear aromatic compounds to produce a cooled gaseous olefinic hydrocarbon stream having a reduced concentration of polynuclear aromatic compounds and a rich liquid absorption stream having a temperature greater than about 120° F.;

(b) recovering said cooled gaseous olefin-containing hydrocarbon stream having a reduced concentration of polynuclear aromatic compounds;

(c) cooling at least a portion of said rich liquid absorption stream from step (a) to provide at least a portion of said cold lean liquid absorption stream;

(d) separating at least a portion of said rich liquid absorption stream from step (a) to produce a stream comprising polynuclear aromatic compounds and a stream having a reduced concentration of polynuclear aromatic compounds; and (e) introducing said stream having a reduced concentration of polynuclear aromatic compounds from step (d) into said countercurrent vapor-liquid absorption zone.

11. A process for cooling a hot vapor effluent of a hydrocarbon dehydrogenation zone having a temperature greater than about 200° F. and comprising normally gaseous olefinic hydrocarbons, trace polynuclear aromatic compounds and trace mononuclear aromatic compounds and removing trace quantities of polynuclear aromatic compounds from said hot vapor effluent which process comprises:

(a) contacting said hot vapor effluent of a hydrocarbon dehydrogenation zone in a countercurrent vapor-liquid absorption zone with a cold lean liquid absorption stream having a temperature less than said hot vapor effluent to cool said hot vapor effluent to a temperature less than about 120° F. and to absorb at least a portion of said trace polynuclear aromatic compounds to produce a cooled gaseous olefinic hydrocarbon stream having a reduced concentration of polynuclear aromatic compounds and comprising trace mononuclear aromatic compounds and a rich liquid absorption stream having a temperature greater than about 120° F.;

(b) compressing and cooling said cooled gaseous olefin-containing hydrocarbon stream having a reduced concentration of polynuclear aromatic compounds and comprising trace mononuclear aromatic compounds to produce a liquid stream comprising mononuclear aromatic compounds and a gaseous olefin-containing hydrocarbon stream having a reduced concentration of polynuclear aromatic compounds;

(c) introducing said liquid stream comprising mononuclear aromatic compounds from step (c) into said countercurrent vapor-liquid absorption zone;

(d) recovering said gaseous olefin-containing hydrocarbon stream having a reduced concentration of polynuclear aromatic compounds from step (b);

(e) cooling at least a portion of said rich liquid absorption stream from step (a) to provide at least a portion of said cold lean liquid absorption stream;

(f) separating at least a portion of said rich liquid absorption stream from step (a) to produce a stream comprising polynuclear aromatic compounds and a stream having a reduced concentration of polynuclear aromatic compounds; and (g) introducing said stream having a reduced concentration of polynuclear aromatic compounds from step (f) into said countercurrent vapor-liquid absorption zone.

* * * * *